(12) United States Patent
Greenberg et al.

(10) Patent No.: US 11,302,430 B1
(45) Date of Patent: *Apr. 12, 2022

(54) COMPUTING SYSTEM FOR GENETIC DATABANK APPLICATION

(71) Applicant: Allscripts Software, LLC, Raleigh, NC (US)

(72) Inventors: Eyal Greenberg, Meitar (IL); Shiri Ben-Tal, Omer (IL); Joel Diamond, Pittsburgh, PA (US); Assaf Halevy, Pittsburgh, PA (US)

(*) Notice: Subject to any disclaimer, the term of this patent is extended or adjusted under 35 U.S.C. 154(b) by 116 days.

This patent is subject to a terminal disclaimer.

(21) Appl. No.: 16/899,892

(22) Filed: Jun. 12, 2020

Related U.S. Application Data

(63) Continuation of application No. 15/639,062, filed on Jun. 30, 2017, now Pat. No. 10,685,744.

(51) Int. Cl.
| | |
|---|---|
| G16H 10/60 | (2018.01) |
| G06F 16/178 | (2019.01) |
| G16B 50/00 | (2019.01) |
| G16B 20/00 | (2019.01) |
| G06F 3/048 | (2013.01) |

(52) U.S. Cl.
CPC ......... G16H 10/60 (2018.01); G06F 16/1794 (2019.01); G16B 50/00 (2019.02); G06F 3/048 (2013.01); G16B 20/00 (2019.02)

(58) Field of Classification Search
CPC ........ G16H 10/60; G16H 20/30; G16H 50/20; G16H 10/65; G16H 80/00; G16H 10/40; G16H 15/00; G16H 50/30; G16H 10/20; G16H 40/63; G16H 50/70; G06F 19/30; G06Q 50/24; G06Q 50/22
See application file for complete search history.

(56) References Cited

U.S. PATENT DOCUMENTS

| | | |
|---|---|---|
| 5,779,634 A | 7/1998 | Ema et al. |
| 5,966,712 A | 10/1999 | Sabatini et al. |
| 7,062,076 B1 | 6/2006 | Osborne et al. |
| 7,529,685 B2 | 5/2009 | Davies et al. |

(Continued)

OTHER PUBLICATIONS

"Notice of Allowance and Fees Due for United States U.S. Appl. No. 15/639,062", dated Feb. 7, 2020, 9 pages.

*Primary Examiner* — Joseph D Burgess
(74) *Attorney, Agent, or Firm* — Calfee, Halter & Griswold LLP

(57) ABSTRACT

Described herein are various technologies pertaining to storing and transmitting formatted genetic test results. A server computing device receives genetic test results from several genetics laboratories, where the genetic test results are in different formats. The server computing device formats each of the genetic test results such that the resultant formatted genetic test results have a uniform format. The server computing device receives a query from a client computing device that is displaying a graphical user interface (GUI) of an electronic health records application (EHR), and searches over the formatted genetic test results to generate search results, wherein the query includes an identifier for a patient whose medical record is being displayed in the GUI of the EHR. The server computing device transmits the search results to the client computing device, whereupon the search results are displayed on the display of the client computing device.

20 Claims, 5 Drawing Sheets

(56) References Cited

U.S. PATENT DOCUMENTS

| | | |
|---|---|---|
| 7,698,154 B2 | 4/2010 | Marchosky |
| 2002/0128860 A1 | 9/2002 | Leveque et al. |
| 2002/0179097 A1 | 12/2002 | Atkins |
| 2005/0026117 A1 | 2/2005 | Judson et al. |
| 2007/0027636 A1 | 2/2007 | Rabinowitz |
| 2008/0071582 A1 | 3/2008 | Fernandez |
| 2013/0185096 A1* | 7/2013 | Giusti .................... G06Q 50/24 705/3 |

* cited by examiner

COMPUTING SYSTEM FOR GENETIC DATABANK APPLICATION

RELATED APPLICATIONS

This application is a continuation of U.S. patent application Ser. No. 15/639,062 ("the '062 application"), filed on Jun. 30, 2017, and entitled "COMPUTING SYSTEM FOR GENETIC DATABANK APPLICATION". The '062 application is related to U.S. patent application Ser. No. 15/433,756, filed on Feb. 15, 2017, and entitled "GRAPHICAL USER INTERFACE FOR PRESENTING TESTING SUGGESTIONS". The '062 application is also related to U.S. patent application Ser. No. 15/231,971, filed on Aug. 9, 2016, and entitled "COMPUTER-EXECUTABLE APPLICATION THAT IS CONFIGURED TO PROCESS CROSS-CLINICAL GENOMICS DATA", which claims priority to U.S. Provisional Patent Application No. 62/300,896, filed on Feb. 28, 2016, and entitled "COMPUTING SYSTEM THAT PRESENTS DATA BASED UPON PANOMICS". The entireties these applications are incorporated herein by reference.

BACKGROUND

Conventionally, there is no suitable technical solution that facilitates convenient sharing of genetic data. This has led to "genomic islands," where large quantities of genetic data are consolidated in several discrete sources that cannot interoperate with one another. Genomic islands can be a hindrance to treatment of a patient when different genetic test results are scattered among different sources. Genomic islands can also be a hindrance to genetic research, which often requires larges amounts of genetic data. In order for a healthcare worker to gain access to the results of all genetic tests a patient has undergone, the healthcare worker must contact each genetic laboratory for the results individually. Sometimes the healthcare worker must rely on the patient to bring in a print-out copy of the genetic test results. This can be problematic, as genetic laboratories can move to different locations, go out of business, etc. Additionally, genetic test results from different genetic tests can be presented in a variety of different formats, such as PDF, JSON, XML, VCF, etc., which can make it difficult to analyze large sets of genetic data.

Electronic health record applications (EHRs) are computer-executable applications that are configured to assist healthcare workers with providing care to patients. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve data from a patient record maintained by an EHR to relatively quickly ascertain problems being experienced by the patient, medications currently being taken by the patient, and so forth. EHRs, however, are currently ill-equipped to handle genetic test results from genetic laboratories. In other words, conventionally there is no suitable technology that allows for an EHR (or other application) to provide a healthcare worker with genetic test results from arbitrary laboratories.

SUMMARY

The following is a brief summary of subject matter that is described in greater detail herein. This summary is not intended to be limiting as to the scope of the claims.

Described herein are various technologies pertaining to computer-executable applications that are well-suited for use in a healthcare environment. More specifically, described herein are various technologies pertaining to a computer-executable genetic databank application that can receive genetic test results from genetic laboratories, where the genetic test results are formatted in a variety of different formats. The genetic databank application can reformat these genetic test results into a uniform data format, and store the (formatted) genetic test results in a data repository. The genetic databank application can also transmit formatted genetic test results to a client computing device based on an identifier for a patient. In an exemplary embodiment, the genetic databank application can also transmit formatted genetic test results for a plurality of patients based on the name of a genetic disorder or genetic variant. In another embodiment, the genetic databank application can transmit formatted genetic test results to a supplement application for further analysis or processing, wherein the supplement application is configured to execute alongside an EHR and is further configured to provide information to a healthcare worker that is supplemental to what is provided to the healthcare worker by way of the EHR.

As will be described in greater detail herein, the genetic databank application may be separate from the EHR; the genetic databank application (or a graphical user interface (GUI) for the genetic databank application) can be launched based upon healthcare worker interaction with the EHR. In another exemplary embodiment, the genetic databank application can be incorporated directly into an EHR as an EHR module.

The genetic databank application described herein provides various advantages to healthcare workers over conventional technologies. The application solves the problem of "genetic islands" by providing a common repository for genetic test results, where genetic test results from multiple laboratories (i.e., genetic laboratories) can be retained and queried. Furthermore, since the genetic test results can be retained in a data store indefinitely, a healthcare worker can access to genetic tests conducted over a patient's lifetime. For example, the healthcare worker can access results for a genetic test conducted when a patient was a child, when the patient was middle-aged, and when the patient was elderly. Having all of this information available at the point of care can be useful in devising care plans for a patient.

In addition, supplement applications can be configured to interface with the genetic databank application, wherein the supplement applications can perform numerous functions using the genetic data. The genetic databank application can also provide advantages over technologies used in conventional genetic laboratories. For example, healthcare workers can access formatted genetic test results via the genetic databank application instead of having to contact a genetic laboratory individually each time access to genetic test results is desirable. This can result in cost-savings for genetic laboratories. Additionally, the genetic databank application can benefit researchers by enabling convenient access to a large amount of genetic test results in a predefined format, making it easy for researchers to perform data analysis on the genetic test results without having to first transform test results into a common format.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
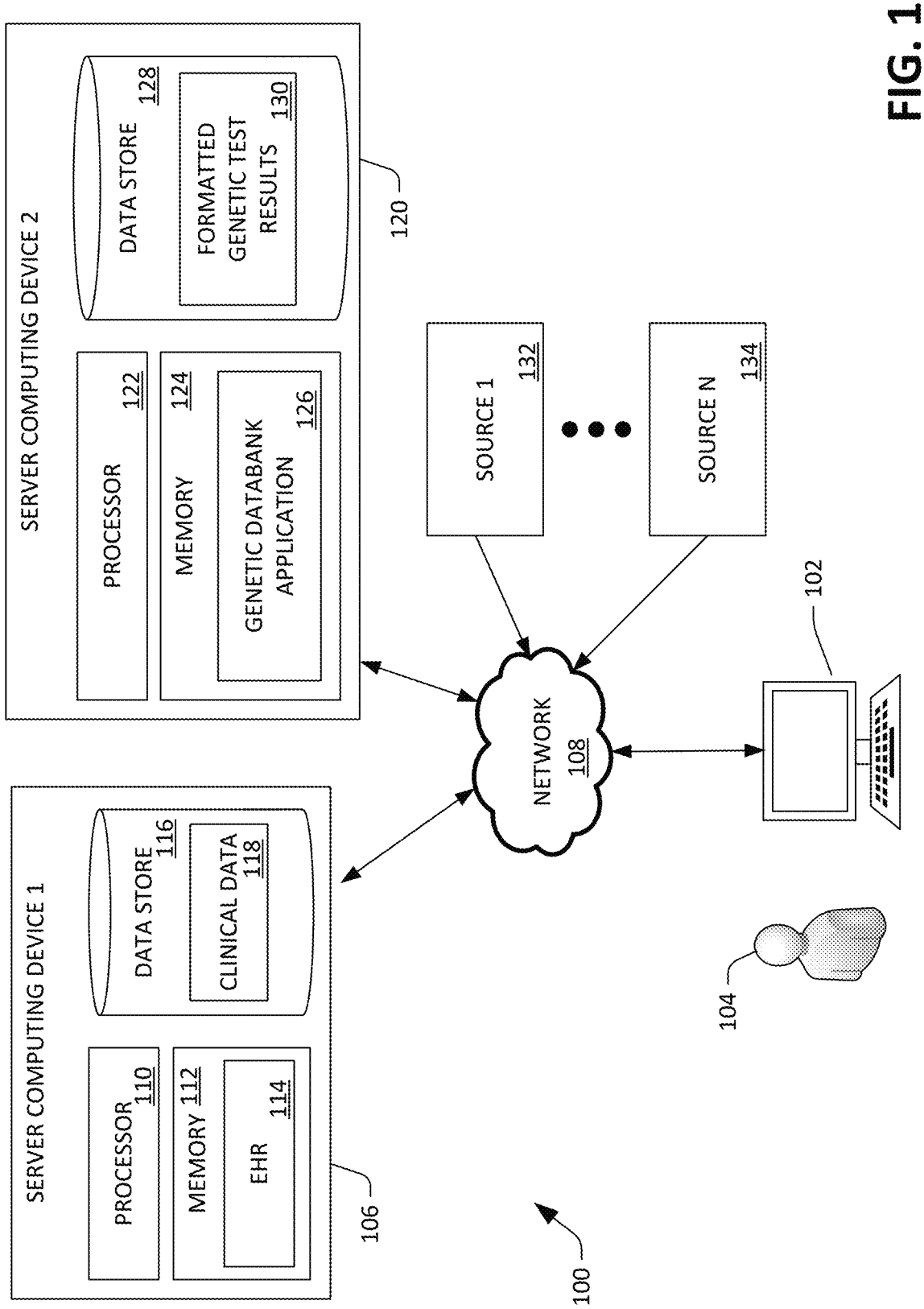
FIG. 1 is a functional block diagram of an exemplary system that facilitates receiving, storing, and transmitting formatted genetic test results.

Various technologies pertaining to formatting genetic test results in a uniform format, storing the formatted genetic test results, and transmitting the formatted genetic test results are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary system 100 that facilitates storing and transmitting formatted genetic test results is illustrated. The system 100 includes a client computing device 102 operated by a healthcare worker 104 (e.g., a clinician). The client computing device 102 may be any suitable type of computing device, including a mobile telephone, a laptop computing device, a desktop computing device, a tablet computing device, etc. The healthcare worker 104 may be providing care to a patient (not shown).

The system 100 additionally includes a first server computing device 106 that is in communication with the client computing device 102 by way of a network 108 (e.g., the Internet and/or an intranet). The first server computing device 106 includes a processor 110 and memory 112, wherein the memory 112 has an EHR 114 loaded therein. The EHR 114 is configured to perform a variety of tasks related to patient care in a healthcare facility (e.g., patient intake, prescription generation, patient record creation and maintenance, etc.). The first server computing device 106 also includes a data store 116 that comprises clinical data 118 about patients, wherein the clinical data 118 is maintained by the EHR 114. The clinical data 118 can include electronic health records, claims data, patient/disease registries data, health surveys data, and/or clinical trials data.

For instance, electronic health records include, but are not limited to including, administrative and demographic information, diagnosis, treatment, prescription drugs, laboratory tests, physiological monitoring data, hospitalization, patient insurance, etc. Administrative information includes hospital discharge data (e.g., reported to a government agency). Claims data describes billable interactions (insurance claims) between insured patients and the healthcare delivery system, and can include four general categories: 1) inpatient; 2) outpatient; 3) pharmacy; and 4) enrollment. Patient/disease registries data includes data generated by clinical information systems that track data for certain chronic conditions, such as Alzheimer's Disease, cancer, diabetes, heart disease, and asthma. Health surveys data includes data from national surveys pertaining to common chronic conditions. Clinical trials data includes data generated during conduction of clinical trials.

The system 100 further comprises a second server computing device 120 that is in communication with the client computing device 102 and the first sever computing device 106 by way of the network 108. The second sever computing device 120 comprises a processor 122 and memory 124, wherein the memory has a genetic databank application 126 loaded therein that is executed by the processor 122. Further, the second server computing device 120 comprises a data store 128 that retains formatted genetic test results 130 for a plurality of patients, wherein there is at least some overlap between patients corresponding to the clinical data 118 in the data store 116 of the first server computing device 106 and patients corresponding to the formatted genetic test results 130 in the data store 128 of the second server computing device 120.

The system 100 further comprises a plurality of data sources 132-134, wherein the data sources 132-134 can be sources of genetic test results. In an example, the data sources 132-134 can be computing devices at genetic laboratories, wherein the computing devices retain genetic test results for patients who have been tested at the genetic laboratories. As genetic test results from the data sources 132-134 may be presented in different formats (e.g., PDF, JSON, XML, VCF, HTML, etc.), the genetic databank application 126 can be configured to recognize genetic test results in a variety of different formats.

Generally, the genetic databank application 126 is configured to receive genetic test results for a patient from any of the data source 132-134 (e.g., a computing device at a genetic laboratory) by way of the network 108. Responsive to receiving the genetic test results, the genetic databank application 126 is configured to format the genetic test results in a uniform format to generate formatted genetic test results 130. In other words, regardless of the format of the incoming genetic test results, the formatted genetic test results will have a format that is common to all genetic test results retained in the data store 128. The genetic databank application 126 can utilize any suitable technology for formatting genetic test results, including mapping entries to one or more schemas, using transformation scripts, etc.

The format is configured so as to allow extraction and manipulation of certain (predefined) elements of genetic test results. In a non-limiting example, the format comprises the locations of genetic variations in the genome of a patient and a diagnosis based on these genetic variations. The genetic databank application 126 stores the formatted genetic test results 130 in the data store 128. Subsequent to storing the formatted genetic test results 130, the genetic databank application 126 is configured to transmit the formatted genetic test results 130 to the client computing device 102. For example, the genetic databank application 126 can be configured to transmit formatted genetic test results 130 to the client computing device 102 for presentation to the healthcare worker 104. Additionally, the genetic databank application 126 can be configured to transmit formatted genetic test results responsive to receipt of a query from the client computing device 102. For example, the query received from the client computing device 102 can specify the name of a genetic disorder, and the databank application 126 search the formatted genetic test results 130 based upon the name of the genetic disorder and generate search results, where the search results include a list of patients who have been diagnosed with the genetic disorder. The genetic databank application 126 can then transmit the search results to the client computing device 102.

Exemplary operation of the system 100 is now set forth. A genetic test for a genetic disorder for a patient can be conducted at a genetic laboratory, the results of which are available from one of the data sources 132-134 (e.g., the data source 132). In a non-limiting example, the genetic test results can be for familial hypercholesterolemia (FH), a genetic disorder that affects over 10 million people and can be traced to several specific mutations in the human genome. The data source 132 can generate a first application programming interface (API) call by way of the network 108. In an embodiment, the data source 132 generates the first API call via a web page. In another embodiment, the data source 132 has a dedicated application being executed that generates the first API call. The first API call can comprise the genetic test results for the patient. The genetic test results can be in a variety of different formats. In non-limiting examples, the genetic test results can be in PDF, JSON, XML, VCF, or HTML format.

The first API call can be an HTTP/s request. Accordingly, the genetic databank application 126 may detect the first API call by monitoring a port for the HTTP/s request. Responsive to detecting the first API call, the genetic databank application 126 can format the genetic test results in accordance with a data model to generate formatted genetic test results. The data model is designed so as to facilitate analysis of the data included therein. As the genetic test results can be in a plurality of formats (PDF, JSON, XML, VCF, HTML, etc.), the genetic databank application 126 is configured to recognize each format in the plurality of formats and incorporate the contents of the genetic test results into the data model. In a non-limiting example, the data model can comprise the name of the genetic test, the date of the genetic test, the institution responsible for the genetic test, the name of the patient, names of any variations in the patient's genome that have been discovered by the genetic test, and the presence or absence of any genetic disorders tested by the genetic test. Responsive to formatting the genetic test results using the data model, the genetic databank application 126 can store the formatted genetic test results in the data store 128.

It is understood that the previously described steps may be repeated a plurality of times for a plurality of patients for a plurality of genetic tests. Hence, the data store 128 may contain formatted genetic test results 130 for a plurality of patients.

Subsequent to storing the formatted genetic test results 130 for the patient, the healthcare worker 104 may be providing care to a patient who has previously been subject to a genetic test. The client computing device 102 can receive user credentials from the healthcare worker 104, and can transmit the user credentials to the first server computing device 106 for authentication. The EHR 114 can authenticate the healthcare worker 104, thereby providing the healthcare worker 104 with access to at least some of the clinical data 118. In an embodiment, the EHR can include a graphical user interface (GUI) that displays at least some of the clinical data 118 to the healthcare worker 104 on a display of the client computing device 102. The GUI can also include a selectable button that, when selected, generates a second API call via an HTTP/s request. In another embodiment, the second API call can be generated automatically when the EHR 114 authenticates the healthcare worker 104. The second API call can comprise an identifier for the patient.

The genetic databank application 126 detects the second API call by monitoring a second port for the HTTP/s request. Responsive to detecting the second API call, the genetic databank application 126 executes a search over the formatted genetic test results 130 retained in the data store 128 based on the identifier for the patient to generate search results. The search results comprise a subset of the formatted genetic test results 130. When the patient has been subject to more than one genetic test, the search results can comprise formatted genetic test results for each genetic test result transmitted to the second server computing device 120 by the plurality of data sources 132-134. Responsive to generating the search results, the genetic databank application 126 can transmit data to the client computing device 102, wherein the data causes the search results to be presented to the healthcare worker 104. In an example, the search results can be depicted in a GUI of the EHR. In another example, the search results can be depicted in a GUI for the genetic databank application 126, which can be displayed beside the GUI of the EHR.

The client computing device 102 may include a display and has an application thereon that communicates with the EHR 114 executing on the first server computing device 106. Such application may be an application dedicated to the EHR 114, a browser, or other suitable application. Additionally, the client computing device 102 has an application executing thereon that is in communication with the genetic databank application 126, wherein such application may have a GUI. Again, such application may be dedicated to the genetic databank application 126, may be a browser, etc. The GUI for the application in communication with the EHR 114 may be displayed simultaneously with the GUI for the application that is in communication with the genetic databank application 126.

In an exemplary embodiment where the EHR 114 is configured with a module designed to receive genetic information, the genetic databank application 126 can be configured to allow the healthcare worker 104 to send the formatted genetic test results to the EHR 114 by way of the network 108.

As noted previously, the genetic databank application 126 can be configured to search based on identifiers other than a patient identifier. In a non-limiting example, the identifier can comprise the name of a genetic disorder. The healthcare worker 104 may want to view all of the formatted genetic test results retained in the data store 128 for a particular genetic disorder. For example, the disorder can be FH. The EHR 114 can generate a third API call via an HTTP/s request, wherein the third API call comprises the name of a genetic disorder. The genetic databank application 126 may detect the third API call. Responsive to detecting the third API call, the genetic databank application 126 can execute a second search over the formatted genetic test results 130 retained in the data store 128 based on the identifier for the genetic disorder for the patient to generate second search results. The second search results comprise a plurality of formatted genetic test results, wherein each genetic test result in the plurality of formatted genetic test results is for the genetic disorder identified by the identifier. Responsive to generating the second search results, the genetic databank application 126 can transmit the second search results to a client computing device 102 for presentment to the healthcare worker 104 on the display of the client computing device 102.

Figure 2:
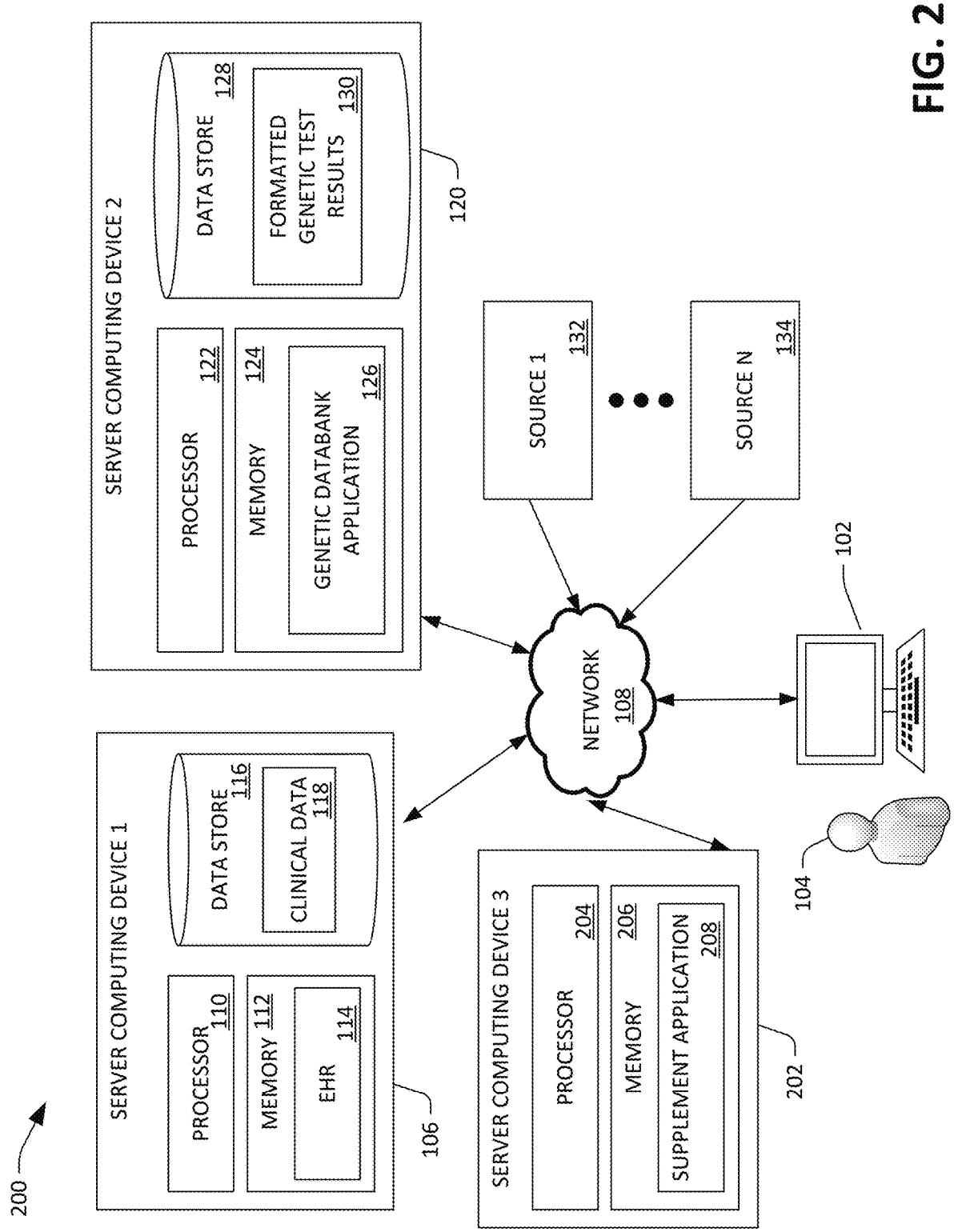
FIG. 2 is a functional block diagram of an exemplary system that facilitates transmitting formatted genetic test results to a supplement application.

With reference to FIG. 2, an exemplary system 200 that facilitates transmitting formatted genetic test results to a supplement application is illustrated. As noted above, supplement applications provide functionality that is not normally included in an EHR. In an example, a supplement application can be configured to calculate the number of patients in a population that share a genetic disorder with a current patient. In another example, a supplement application can be configured to output a list of patients, each patient in the list of patients sharing a genetic disorder. In another example, a supplement application can be configured to receive genetic test results and perform analysis on the genetic test results.

The exemplary system 200 comprises the components of the system 100, and further comprises a third server computing device 202 that is in communication with the client computing device 102, the first server computing device 106, and the second server computing device 120 by way of the network 108. The third server computing device 202 comprises a processor 204 and memory 206, wherein the memory 206 has a supplement application 208 loaded therein that is executed by the processor 204. The third server computing device 202 can include a data store (not shown), wherein the data store includes data that is accessible to the supplement application 208.

In the exemplary system 200, the supplement application 208 is configured to interface with the genetic databank application 126 (e.g., rather than the EHR 114 interfacing with the genetic databank application 126). In such an example, the supplement application 208 may receive data that identifies a patient from the EHR 114 (directly or indirectly). For instance, when the EHR 114 transmits at least a portion of an electronic medical record for a patient to the client computing device 102, the EHR 114 can transmit an identifier for the patient to the supplement application 208. Alternatively, the client computing device 102, responsive to receiving at least a portion of the electronic medical record for a patient from the EHR 114, can transmit an identifier for the patient to the supplement application 208. In other examples, the supplement application 208 can receive an identifier for a genetic disorder from the EHR 114 and/or the client computing device 102.

The supplement application 208, responsive to receiving the above-described identifier(s) from the EHR 114 and/or the client computing device 102, can transmit the identifier(s) to the second server computing device 120 for receipt by the genetic databank application 126. Responsive to receiving these identifier(s), the genetic databank application 126 executes a search over the formatted genetic test results 130 retained in the data store 128 based on the identifier(s) to generate search results (which may comprise records that are representative of a plurality of genetic test results). Responsive to generating the search results, the genetic databank application 126 can transmit the search results to the supplement application 208 by way of the network 108. The supplement application 208 can then use the formatted genetic data in the search results to perform functions that it is configured to perform.

Figure 3:
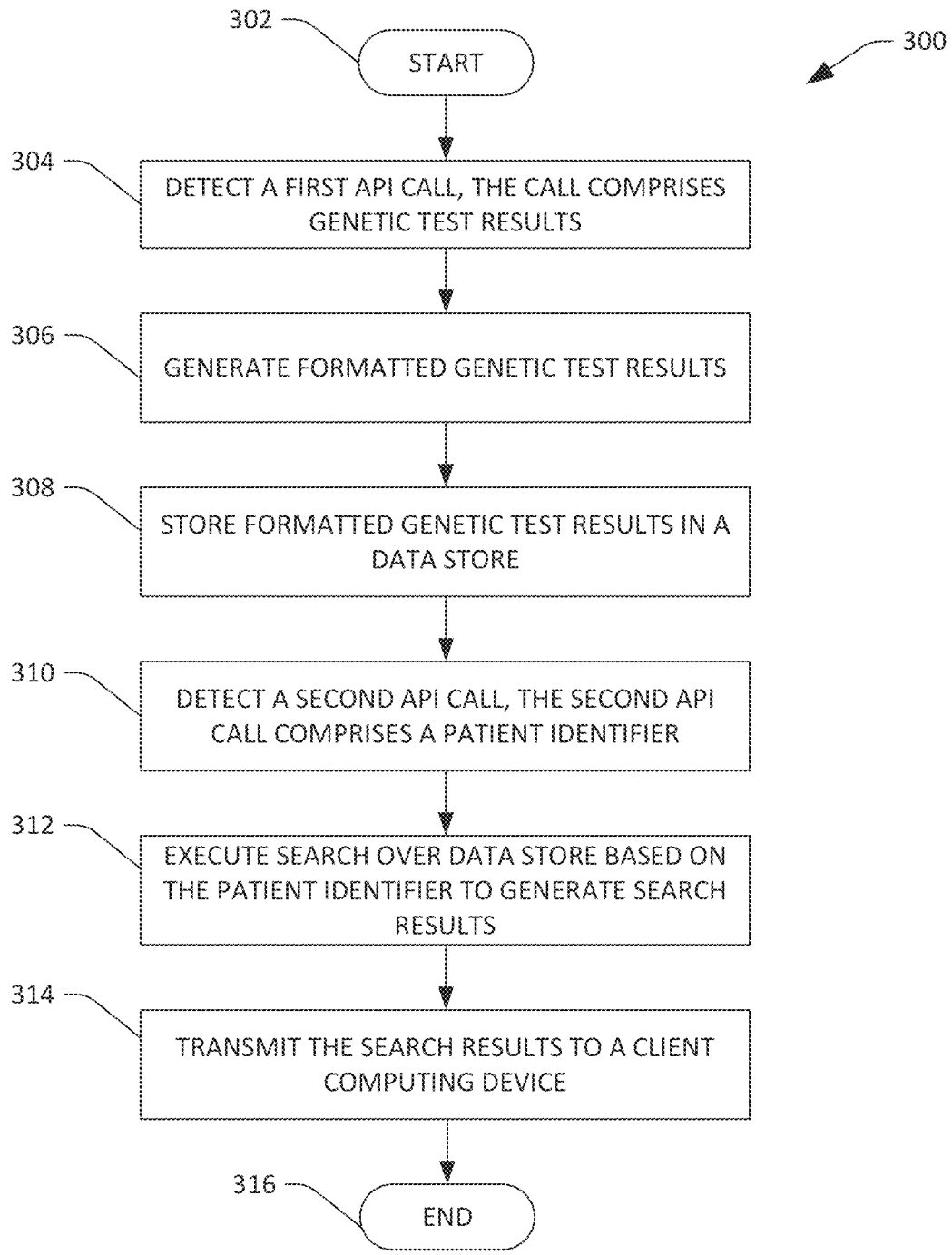
FIG. 3 is a flow diagram illustrating an exemplary methodology for receiving, storing, and transmitting formatted genetic test results for a patient.
Figure 4:
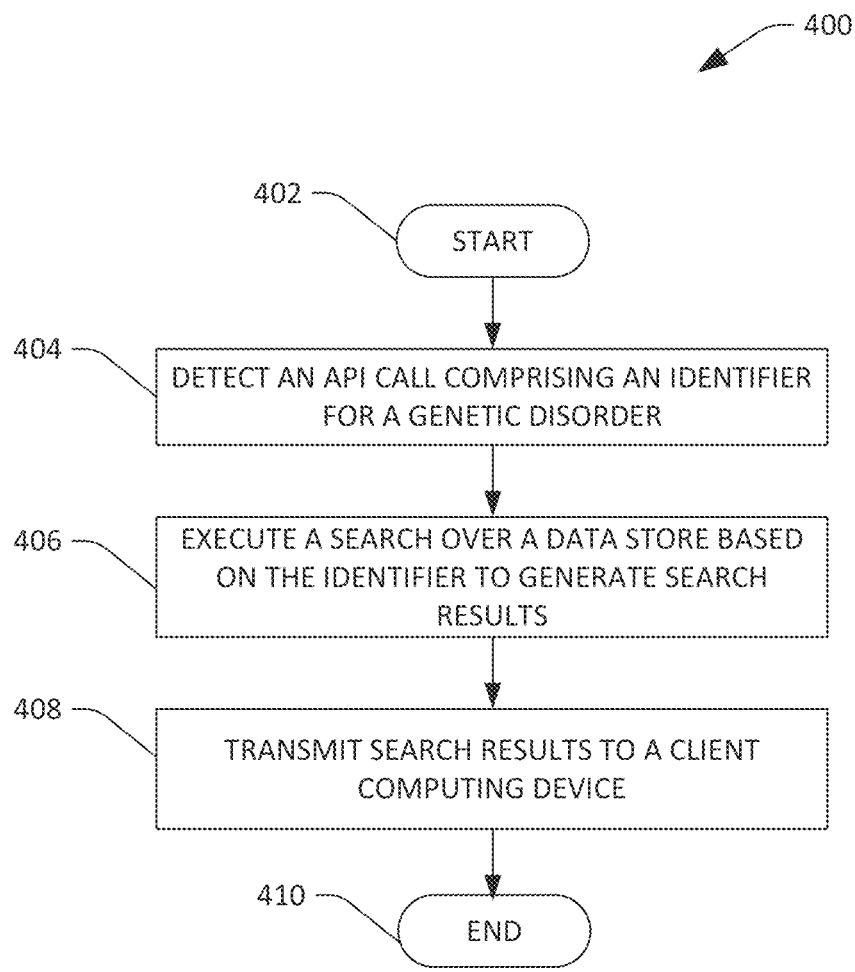
FIG. 4 is a flow diagram illustrating an exemplary methodology for receiving a plurality of genetic test results.

FIGS. 3-4 illustrate exemplary methodologies relating to storing and transmitting formatted genetic test results. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 3, an exemplary methodology 300 that facilitates storing and transmitting formatted genetic test results for a patient is illustrated. The methodology 300 is executed at a server computing device that executes the genetic databank application 126. The methodology 300 begins at 302, and at 304 a first API call comprising genetic test results for a genetic disorder for a patient is detected. The first API call may be an HTTP/s request, and detecting the first API call may comprise monitoring a port for the HTTP/s request. The first API call may originate from a computing device at a genetic laboratory performing genetic tests. For instance, as described above, a computing device at a genetic laboratory can output the HTTP/s request responsive to a geneticist at a genetic laboratory selecting a button in a GUI. The genetic test results may be in PDF, JSON, XML, VCF, HTML, or another file format used by the genetic laboratory.

At 306, the genetic test results are formatted according to a data model to generate formatted genetic test results. The formatted genetic test results are uniform regardless of the format in which the genetic test results were received. At 308, the formatted genetic test results for the patient are stored in a data store. It is understood that the previously mentioned steps may be repeated a plurality of times for a plurality of genetic test results, such that the data store stores a plurality of formatted genetic test results for several patients.

At 310, sometime after the formatted genetic test results are stored in the data store, a second API call generated by an EHR (as described above) is received. In another embodiment, the second API call may be generated directly by a client computing device. In yet another embodiment, the second API call may be generated by a supplement application executing on a server computing device. The second API call comprises an identifier for the patient whose formatted genetic test results were stored at 308. The second API call may be an HTTP/s request, and detecting the second API call may comprise monitoring a port for the HTTP/s request. It is understood that the patient may be being provided care by a healthcare worker when the second API call is generated. At 312, a search based on the identifier is conducted over the data store to generate search results. The search results comprise a subset of the formatted genetic test results stored in the data store at 308. When the patient has undergone more than one genetic test, the search results can comprise formatted genetic test results for each genetic test that the patient has undergone. At 314, the search results are transmitted to a client computing device for presentation on a display of the client computing device. In another embodiment, the search results can be transmitted to a server computing device executing a supplement application. The methodology completes at 316.

Referring now to FIG. 4, an exemplary methodology 400 that facilitates transmitting a plurality of genetic test results is illustrated. Each genetic test result in the plurality of genetic test results can be for a particular genetic disorder. It is understood that the methodology 400 can occur after the methodology 300 has been performed. The methodology 400 beings at 402, and at 404, an API call comprising a second identifier is detected, where the second identifier is for a genetic disorder. In an embodiment, the API call may originate from an EHR. In another embodiment, the API call may originate from a client computing device. In yet another embodiment, the API call may originate from a supplement application. In a non-limiting example, the API may comprise an identifier for a genetic disorder. For example, the genetic disorder may be familial hypercholesterolemia. The API call may be an HTTP/s request, and detecting the third API call may comprise monitoring a port for the HTTP/s request.

At 406, a second search is executed over a data store based on the second identifier to generate second search results. The second search results can comprise a plurality of formatted genetic test results, wherein each formatted genetic test result in the plurality of formatted genetic test result pertains to the genetic disorder identified by the second identifier. At 408, the second search results are transmitted to a client computing device for presentation on a display of the client computing device. In another embodiment, the second search results are transmitted to a supplement application executing on a server computing device. As the second search results are in a uniform data model, a healthcare worker may then easily perform analysis on the data contained in the second search results. In a non-limiting example, a healthcare worker can examine the second search results to determine how frequently the genetic test yields particular results. The methodology completes at 310.

Figure 5:
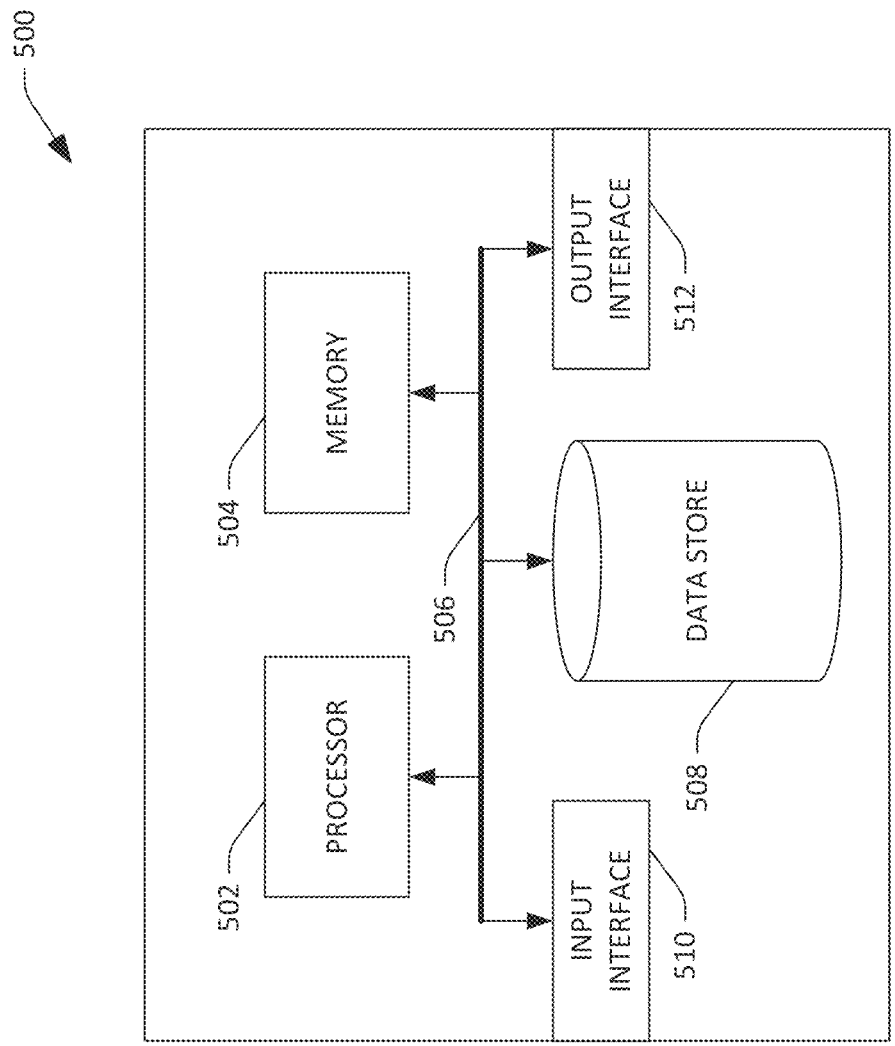
FIG. 5 is an exemplary computing system.

Referring now to FIG. 5, a high-level illustration of an exemplary computing device 500 that can be used in accordance with the systems and methodologies disclosed herein is illustrated. For instance, the computing device 500 may be used in a system that executes a genetic databank application. By way of another example, the computing device 500 can be used in a system that facilitates the storage and transmission of formatted genetic test results. The computing device 500 includes at least one processor 502 that executes instructions that are stored in a memory 504. The instructions may be, for instance, instructions for implementing functionality described as being carried out by one or more components discussed above or instructions for implementing one or more of the methods described above. The processor 502 may access the memory 504 by way of a system bus 506. In addition to storing executable instructions, the memory 504 may also store clinical data, genetic testing data, rules, etc.

The computing device 500 additionally includes a data store 508 that is accessible by the processor 502 by way of the system bus 506. The data store 508 may include executable instructions, genetic test results, clinical data, rules, etc. The computing device 500 also includes an input interface 510 that allows external devices to communicate with the computing device 500. For instance, the input interface 510 may be used to receive instructions from an external computer device, from a user, etc. The computing device 500 also includes an output interface 512 that interfaces the computing device 500 with one or more external devices. For example, the computing device 500 may display text, images, etc. by way of the output interface 512.

It is contemplated that the external devices that communicate with the computing device 500 via the input interface 510 and the output interface 512 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 500 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 500 may be a distributed system. Thus, for instance, several devices may be in communication by way of a network connection and may collectively perform tasks described as being performed by the computing device 500.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A server computing device comprising:
   a processor;
   memory storing a genetic databank application that, when executed by the processor, causes the processor to perform acts comprising:
     detecting a first application programming interface (API) call generated by a source computing device, wherein the first API call comprises genetic test results of a patient;
     responsive to detecting the first API call, formatting the genetic test results in accordance with a data model to generate formatted genetic test results;
     responsive to generating the formatted genetic test results, storing the formatted genetic test results in a data store;
     subsequent to storing the formatted genetic test results in the data store, detecting a second API call generated by a computing device, wherein the second API call comprises an identifier for the patient;
     responsive to detecting the second API call, executing a search over the data store to generate search results, the search being based upon the identifier for the patient comprised by the second API call, and further wherein the search results comprise the formatted genetic test results; and
     responsive to generating the search results, transmitting the formatted genetic test results to the computing device, wherein the computing device causes the formatted genetic test results to be displayed within a graphical user interface (GUI) for the genetic databank application shown on a display.

2. The server computing device of claim 1, wherein the genetic test results of the patient include data that is indicative of whether the patient has a genetic disorder.

3. The server computing device of claim 1, wherein the genetic test results are in PDF, JSON, XML, VCF, or HTML format when the first API call is detected.

4. The server computing device of claim 1, wherein a GUI for an electronic health records application (EHR) is shown concurrently on the display with the GUI for the genetic databank application.

5. The server computing device of claim 1, wherein a supplement application executing on the computing device causes the computing device to generate the second API call.

6. The server computing device of claim 1, wherein the data store further stores formatted genetic test results for a plurality of patients, the acts further comprising:
   detecting a third API call generated by the computing device, wherein the third API call comprises an identifier for a genetic disorder;
   responsive to detecting the third API call, executing a second search over the data store to generate second search results, the second search being based upon the identifier for the genetic disorder comprised by the third API call, and further wherein the second search results comprise formatted genetic test results for a subset of the plurality of patients, each formatted genetic test result in the subset being for the genetic disorder; and
   responsive to generating the second search results, transmitting the formatted genetic test results for the subset to the computing device for presentation within the GUI for the genetic databank application.

7. The server computing device of claim 1, wherein the computing device is being operated by a healthcare worker when the second API call is detected, wherein the healthcare worker is providing care to the patient.

8. The server computing device of claim 1, wherein the first API call is a first HTTP/s request, wherein detecting the first API call comprises monitoring a first port for the first HTTP/s request, wherein the second API call is a second HTTP/s request, wherein detecting the second API call comprises monitoring a second port for the second HTTP/s request.

9. A method executed by a processor of a server computing device, comprising:
   detecting a first application programming interface (API) call generated by a source computing device, wherein the first API call comprises genetic test results for a patient;
   responsive to detecting the first API call, formatting the genetic test results in accordance with a data model to generate formatted genetic test results;
   responsive to generating the formatted genetic test results, storing the formatted genetic test results in a data store;
   subsequent to storing the formatted genetic test results in the data store, detecting a second API call generated by a supplement application, wherein the second API call comprises an identifier for the patient;
   responsive to detecting the second API call, executing a search over the data store to generate search results, the search being based upon the identifier for the patient comprised by the second API call, and further wherein the search results comprise the formatted genetic test results; and
   responsive to generating the search results, transmitting the formatted genetic test results to the supplement application, wherein the supplement application causes the formatted genetic test results to be displayed within a graphical user interface (GUI) shown on a display.

10. The method of claim 9, wherein the data store further stores formatted genetic test results for a plurality of patients, the method further comprising:
   detecting a third API call generated by the supplement application, wherein the third API call comprises an identifier for a genetic disorder;
   responsive to detecting the third API call, executing a second search over the data store to generate second search results, the second search being based upon the identifier for the genetic disorder comprised by the third API call, and further wherein the second search results comprise formatted genetic test results for a subset of the plurality of patients, each formatted genetic test result in the subset being for the genetic disorder; and
   responsive to generating the second search results, transmitting the formatted genetic test results for the subset to the supplement application for presentation within the GUI.

11. The method of claim 10, wherein the genetic disorder is familial hypercholesterolemia.

12. The method of claim 9, wherein the supplement application executes on a second server computing device, wherein the GUI is shown on a display of a client computing device.

13. The method of claim 9, wherein an electronic health records application (EHR) causes the supplement application to receive the identifier for the patient, wherein the supplement application generates the second API call responsive to receiving the identifier for the patient.

14. The method of claim 9, wherein the supplement application is configured to calculate a number of patients in a population that share a genetic disorder with the patient.

15. The method of claim 9, wherein the first API call is a first HTTP/s request, wherein detecting the first API call comprises monitoring a first port for the first HTTP/s request, wherein the second API call is a second HTTP/s request, wherein detecting the second API call comprises monitoring a second port for the second HTTP/s request.

16. A non-transitory computer-readable storage medium comprising instructions that, when executed by a processor, cause the processor to perform acts comprising:
   detecting a first application programming interface (API) call generated by a computing device of a genetic laboratory, wherein the first API call comprises genetic test results for a patient;
   responsive to detecting the first API call, formatting the genetic test results in accordance with a data model to generate formatted genetic test results;
   responsive to generating the formatted genetic test results, storing the formatted genetic test results in a data store;
   subsequent to storing the formatted genetic test results in the data store, detecting a second API call generated by a supplement application, wherein the second API call comprises an identifier for the patient;
   responsive to detecting the second API call, executing a search over the data store to generate search results, the search being based upon the identifier for the patient comprised by the second API call, and further wherein the search results comprise the formatted genetic test results; and
   responsive to generating the search results, transmitting the formatted genetic test results to the supplement application, wherein the supplement application causes the formatted genetic test results to be displayed within a graphical user interface (GUI) shown on a display.

17. The non-transitory computer-readable storage medium of claim 16, wherein the genetic test results are initially formatted in a first format of the genetic laboratory, wherein the formatted genetic test results are formatted in a second format that is different than the first format.

18. The non-transitory computer-readable storage medium of claim 16, the acts further comprising:
   detecting a third API call generated by a second computing device of a second genetic laboratory, wherein the third API call comprises second genetic test results for the patient;
   responsive to detecting the third API call, formatting the second genetic test for the patient in accordance with the data model to generate second formatted genetic test results; and
   responsive to generating the second formatted genetic test results, storing the second formatted genetic test results in the data store.

19. The non-transitory computer-readable storage medium of claim 16, wherein the formatted genetic test results comprise a location of a genetic variation within a genome of the patient and a diagnosis based upon the genetic variation.

20. The non-transitory computer-readable storage medium of claim 16, wherein the computing device of the genetic laboratory generates the first API call by way of a webpage.

\* \* \* \* \*